United States Patent [19]

Pike

[11] Patent Number: 4,583,551

[45] Date of Patent: Apr. 22, 1986

[54] MULTIPOLAR MEDICAL ELECTRODE

[76] Inventor: Harold Pike, 3747 S. Inca St., Englewood, Colo. 80110

[21] Appl. No.: 672,614

[22] Filed: Nov. 19, 1984

[51] Int. Cl.$^4$ ............................................. A61B 5/04
[52] U.S. Cl. .................................................. 128/640
[58] Field of Search ....................... 128/639, 640, 803

[56] References Cited

U.S. PATENT DOCUMENTS 4,082,087  4/1978  Howson .

Primary Examiner—William E. Kamm
Attorney, Agent, or Firm—Fields, Lewis, Pittenger & Rost

[57] ABSTRACT

A multipolar medical electrode for attachment to the skin of a patient for deriving separate electrical signals from spaced locations indicative of physiological activity is provided. A flexible pad of nonconductive material has a pair of well members which each contain an electrolytic gel to make contact with the patient's skin when an adhesive backing is removed. An electrical connector for connecting the electrode pad to an electrical potential measuring instrument includes a nonconductive body having a pair of spaced conductive prongs connected by wires to the electrical potential measuring instrument. The prongs are inserted respectively through a puncturable membrane in the respective well members, making intimate contact with the electrolytic gel and have a generally box-shaped housing attached to the nonconductive body protects the prongs and slidably engages the outer surfaces of the well members to assist in guiding the prongs into the well members.

17 Claims, 3 Drawing Figures

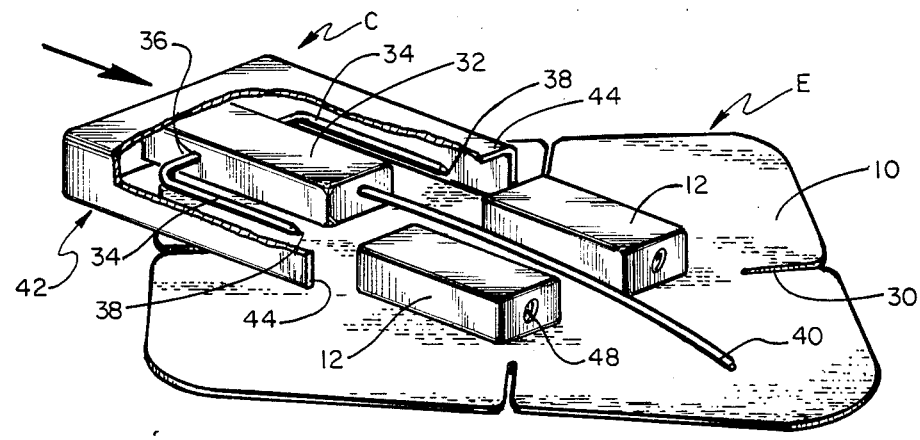
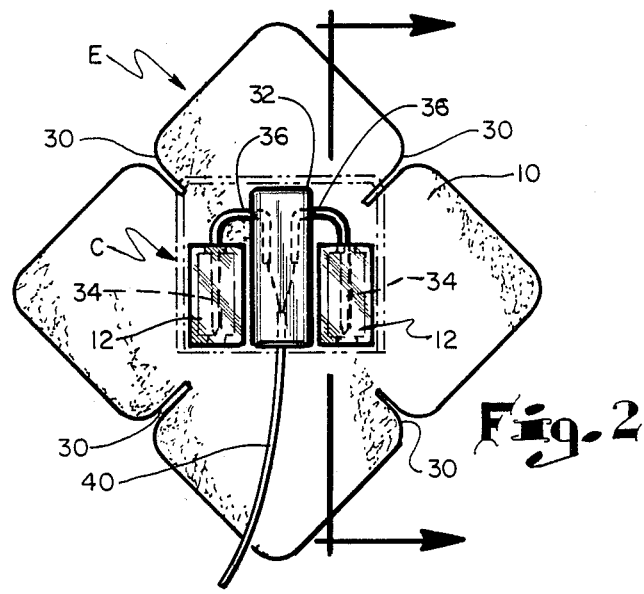
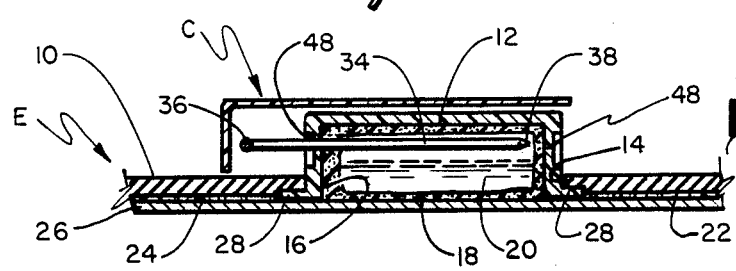

MULTIPOLAR MEDICAL ELECTRODE

Technical Field

This invention relates to multipolar medical electrodes, and more particularly, to multipolar medical electrodes for attachment to the skin of a patient for deriving electrical signals associated with physiological activity. The electrodes are especially suitable for use as electrocardiogram (EKG) electrodes, but can be used to derive signals representing other physiological activity such as electromyographic and electroencephalographic signals.

BACKGROUND ART

A number of arrangements of multipolar medical electrodes for attachment to a patient's skin for deriving electrical signals associated with physiological activity are known in the prior art. Electrodes intended for one-time patient use are considered disposable, while those that can be reused many times are considered permanent.

Conventional permanent medical electrodes are available in several styles, but are generally relatively expensive, must be cleaned carefully between uses, are not self-adhesive, and require an application of electrolytic gel or fluid at the time of each use. Such a permanent multipolar medical electrode is described U.S. Pat. No. 4,082,087 to Howson.

Further, there are a number of single-poled medical electrodes known in the prior art. In order to derive a differential electrical signal, it is typical to use three electrodes. This can be expensive, time consuming, and can lead to electromagnetic interference from the loop formed by the electrode leads, as well as to interaction with electrosurgical equipment. Such a single-poled disposable medical electrode is provided in U.S. Pat. No. 4,126,126 to Bare, et al.

It is desirable that a medical electrode conform well to the skin to provide maximum electrical contact, allow longer wearing time, and ensure patient comfort. Flexible pads of various shapes and configurations have been used to attain conformity with the skin. One such configuration is provided in the above-mentioned Howson patent.

It is also desirable that connections to the electrode be clean, safe, and easily made. For instance, exposed connector prongs can become contaminated by contact with human hands or otherwise, causing a poor electrical connection. If such exposed prongs are pointed, as they often are, there remains a danger of accidentally puncturing the skin of both the technician and the patient. Ease and sureness of connection are also important in the setting in which the electrodes are typically used.

DISCLOSURE OF THE INVENTION

In accordance with the present invention, a multipolar medical electrode is provided for attachment to the skin of a patient for deriving electrical signals associated with physiological activity. This electode includes a thin, flat, flexible pad of nonconductive material having an adhesive on one of its surfaces and at least two spaced well members extending from the other surface, with each well member forming a cavity for containing an electrolytic gel. In operation, a release backing, covering the adhesive surface, is removed and the pad is attached to the skin of the patient by pressing the adhesive surface against the skin, thus bringing the electrolytic gel in the cavities into electrical contact with the skin in at least two spaced locations. A puncturable membrane on each well member is punctured by one of at least two spaced conductive prongs of an electrical connector, thereby making intimate contact with the electrolytic gel. Once the electrode is attached to the skin and the electrical connector is in place, differential electrical signals are derived from the spaced electrodes and transmitted to an electrical potential measuring instrument.

In addition, the pad can include a series of spaced cuts around its periphery and extending inward to divide the pad into sections which substantially conform to the contours of the patient's skin, with the well members being located in a center portion of the pad between the sections. Preferably, the pad is generally rectangular in shape, with four or more spaced cuts around its periphery. The invention further contemplates a porous matrix in each cavity containing the electrolytic gel, the porous material being constructed of either polyethylene foam or other plastic. In addition each of the membranes can include a conductive prong guide means such as a dimple or guide for aligning the conductive prongs for puncturing the membranes.

More particularly, the electrical connector includes a nonconductive body having at least two parallel, spaced, conductive prongs, each having a proximate end embedded in the body and a distal end extending from the body. The connector also includes a like number of connecting wires each having an end connected respectively to the proximate ends of the prongs, and another end connected to the electrical potential measuring means. Advantageously, the body of the connector is sized to just fit between the well members to guide the prongs into the well members as the body is slid between them. More particularly, the body has a width slightly less than the width of the space between the well members, to align the prongs with the conductive prong guide means for ease of entry into the well members.

Preferably, the electrical connector further includes a generally box-shaped housing attached to the body with a top wall spaced from the prongs and extending across them and beyond their distal end to protect them. A pair of side walls depend from the top walls, and are spaced to slidably engage the well members to further assist in guiding the prongs into the well members.

Based on the foregoing, a number of advantages of the present invention are readily apparent. A unique multipolar medical electrode is provided for deriving at least two electrical signals associated with physiological activity. Because it must be attached at only one location on the body, the electrode is cost-effective and convenient to use. An electrode pad is provided which minimizes patient discomfort and allows for longer periods of attachment, while maximizing electrical contact.

The electrical connector body and housing are designed to provide a secure and easily effected joining of the connector with the electrode well members. Furthermore, safety and cleanliness are enhanced by the protection afforded the prongs by the housing.

Additional advantages of this invention will become readily apparent from the description which follows, together with the accompanying drawings.

BRIEF DESCRIPTION OF THE DRAWINGS

FIG. 1 is a perspective view of an electrode pad and connector in accordance with the invention;

FIG. 2 is a top plan view of the electrode pad with the connector attached, the connector housing being shown in dotted lines for clarity of illustration; and FIG. 3 is a horizontal sectional view of the electrode pad, taken along line 3—3 of FIG. 2 showing details of the well construction and insertion of the connector.

BEST MODE FOR CARRYING OUT THE INVENTION

In accordance with the present invention, as depicted in FIG. 1, a disposable electrode member E is provided which includes a thin, flat, generally rectangular flexible electrode pad 10. Two spaced well members 12 extend through spaced openings, such as opening 14 in the pad, as best seen in FIG. 3. Each well member 12 defines a cavity 16 containing a porous gel matrix 18 saturated with an electrolytic gel 20. As shown in FIG. 3, pad 10 includes a first or lower surface 22 having an adhesive layer 24, with a release backing 26 covering the adhesive layer 24, as well as the opening of cavity 16 to contain the gel matrix 20. Conveniently, the lower edges of well members 12 are each formed with an outwardly extending lip 28 which extends under pad 10 at opening 14. The cavity 16 in combination with the release backing 26 provides a moisture-proof enclosure for protecting the electrolyte for extended periods of time. In operation, the release backing is removed and the pad is attached by pressing the adhesive surface against the skin of the patient, thus making contact between the gel and the skin at two spaced locations for deriving two separate electrical signals indicative of physiological activity.

The pad is formed of a thermoplastic material which is flexible, has low moisture absorption, and is electrically nonconductive. Suitable materials include silicone rubber, natural rubber, thermoplastic rubber, polyvinyl chloride, polyurethane, or other flexible polymers.

In the preferred embodiment, the pad 10 is generally rectangular in shape, with four or more spaced cuts 30 spaced around its periphery and extending inward. The cuts 30 are spaced between the corners and serve to divide the pad into sections which can flex independently, allowing the pad to conform to the skin of the patient.

As shown in FIG. 1, an electrical connector C is used in conjunction with the electrode member E for connecting it to an electrical potential measuring instrument. The connector C includes a nonconductive body 32 having a pair of pointed conductive prongs 34 each having a proximate end 36 embedded in the body 32 and a distal pointed end 38 extending therefrom. The body 32 of the connector C is sized to just fit between the well members 12 to guide the prongs 34 into the well members 12 as the body 32 is slid between them the body having a width slightly less than the shortest distance between the well members. An electrical wire 40 is connected to the proximate end 36 of each prong 34, and connects the prongs to an electrical potential measuring instrument.

The electrical connector C further includes a generally box-shaped housing 42 attached to the body 32 with a top wall 44 spaced from the prongs 34 and extending across them and beyond their distal ends 38 to protect them. A pair of side walls 46 depend from the top wall 44 and are spaced to slidingly engage the outer surfaces of the well members 12, as shown, to further assist in guiding the prongs 34 into the well members 12. Thus, the pointed ends 38 of prongs 34 will puncture membranes 48 formed in each end wall of each well member 12 as a dimple having a reduced thickness. As connector C continues to be slid toward the well members 12, the prongs will be pushed into and through gel matrix 18 to make contact with the electrolytic gel 20.

In operation the electrode member E and the electrical connector C are connected by holding the connector body 32 in one hand and the electrode member E in the other hand, then piercing the membranes 48 with the pointed ends 38 of prongs 34, pushing the prongs 34 snugly into the respective gel cavities 12. Because the gel matrix 18, which may be an open-pore polyurethane, is not readily compressible, the insertion of the prongs 34 creates a snug fit which aids in holding the connector C in place, and maintains intimate contact between the gel 20 and the prongs 34, resulting in a secure electrical connection. By providing the dimpled membranes in each end of the well members, the connector can be attached from either side.

The patient's skin is then prepared for attachment of the electrode pad 10 by standard cleaning procedures. The release backing 26 is then removed and the pad 10 is attached to the patient's skin by pressing the adhesive layer or surface 24 against the skin, forcing the gel 20 into intimate contact with the skin.

Based on the foregoing description, a number of worthwhile advantages of the present invention are readily apparent. A multipolar medical electrode capable of deriving more than one electrical signal from spaced points on a single electrode pad is provided. This reduces costs associated with using multiple electrodes to perform the same function. Problems such as electromagnetic interference and interference from electrosurgical equipment are also minimized by using only one electrode. The present invention also offers ease of attachment, as well as a secure electrical connection. The design of the pad allows attachment for a longer period of time with less patient discomfort and a continued secure electrical connection. In addition, safety and cleanliness are enhanced by the protection of the prongs by the connector housing.

This invention has been described in detail with reference to a particular embodiment thereof, but it will be understood that various other modifications can be effected within the spirit and scope of this invention.

I claim:

1. A multipolar medical electrode, attachable to the skin of a patient, for deriving electrical signals associated with physiological activity, said electrode comprising:

a thin, flat, flexible pad of nonconductive material having opposite surfaces with an adhesive on one of said surfaces;

a plurality of spaced well members extending from the other surface of said pad, each well member forming a cavity;

an electrolytic gel in said cavity;

a release backing covering said adhesive surface and enclosing the electrolytic gel within said cavities and being removable for attaching said pad to the skin of the patient by pressing the adhesive on said one surface against the skin to bring the gel in each of said cavities into electrical contact with the skin at spaced locations;

a puncturable membrane on each of said well members; and an electrical connector having a plurality of spaced conductive prongs for respectively puncturing each said membrane to make intimate contact with said electrolytic gel to transmit differential electrical signals to an electrical potential measuring instrument.

2. A medical electrode as claimed in claim 1, further comprising:

a porous matrix in each of said cavities containing said electrolytic gel.

3. A medical electrode as claimed in claim 1, further comprising:

conductive prong guide means formed in each of said membranes for aligning said conductive prongs for puncturing said membranes.

4. A medical electrode as claimed in claim 1, wherein:

said pad has a peripheral surface with a plurality of spaced cuts spaced therearound and extending inwardly to divide said pad into sections, which sections substantially conform to the contours of the patient's skin.

5. A medical electrode as claimed in claim 4, wherein:

said well members are located in a center portion of said pad between said sections.

6. A medical electrode as claimed in claim 1, wherein said electrical connector comprises:

a body of nonconductive material, said prongs being parallel and each having a proximate end embedded in said body and a distal pointed end extending from said body; and a plurality of connecting wires running from said body for connection to the electrical potential measuring means, said connecting wires each having an end connected respectively to said proximate end of one of said prongs.

7. A medical electrode as claimed in claim 6, wherein:

said body of said electrical connector has a width slightly less than the width of the space between said well members to guide said distal ends of said prongs into said conductive prong guide means as said body is slid between said well members.

8. A medical electrode as claimed in claim 7, wherein:

said electrical connector further includes a generally box-shaped housing attached to said body and having:

a top wall extending across said prongs and spaced therefrom; and a pair of side walls depending from said top wall and spaced to slidably engage the outer surfaces of said well members to further assist in guiding said prongs into said well members.

9. A medical electrode as claimed in claim 8, wherein:

said top wall and side walls of said housing extend beyond said distal end of said prongs to protect them.

10. A medical electrode as claimed in claim 6, wherein:

said pad is generally rectangular in shape, having at least four spaced cuts, each beginning at the outer perimeter of said pad and continuing inward toward its center, dividing the pad into sections for conforming said pad to the skin of the patient.

11. A medical electrode as claimed in claim 6, further comprising:

a porous plastic matrix in said cavity containing said electrolytic gel.

12. A medical electrode as claimed in claim 6, further comprising:

a porous polyethylene foam matrix in said cavity containing said electrolytic gel.

13. A medical electrode as claimed in claim 1, further including:

a wall on each of said well members, said puncturable membrane being located in said wall; and conductive prong guide means for aligning said prongs with said membrane.

14. A multipolar medical electrode, attachable to the skin of a patient, for deriving electrical signals associated with physiological activity, said electrode comprising:

a thin, flat, flexible pad of nonconductive material having opposite surfaces with an adhesive on one of said surfaces;

a pair of spaced well members attached to said pad and extending from the other surface thereof, each well member forming a cavity;

an electrolytic gel in said cavity;

a release backing covering said adhesive surface and enclosing the electrolytic gel within said cavities and being removable for attaching said pad to the skin of the patient by pressing the adhesive on said one surface against the skin to bring the gel in each of said cavities into electrical contact with the skin at two spaced locations;

at least one puncturable membrane on each of said well members;

conductive prong guide means formed in each of said membranes for aligning said conductive prongs for puncturing said membranes;

an electrical connector having a body of nonconductive material having a pair of spaced conductive prongs, said prongs being parallel and each having a proximate end embedded in said body and a distal end extending from said body; and a pair of connecting wires running from said body for connection to the electrical potential measuring means, said connecting wires each having an end connected respectively to said proximate end of one of said prongs.

15. A medical electrode as claimed in claim 14, wherein:

said body of said electrical connector has a width slightly less than the width of the space between said well members to guide said distal ends of said prongs into said conductive prong guide means as said body is slid between said well members; and said electrical connector further includes a generally box-shaped housing attached to said body and having:

a top wall extending across said prongs and spaced therefrom, said top wall extending beyond said distal end of said prongs to protect them; and a pair of side walls depending from said top wall and spaced to slidably engage the outer surfaces of said well members to further assist in guiding said prongs into said well members.

16. A medical electrode as claimed in claim 15, wherein:

one of said puncturable membranes is located on each opposite end of each of said well members.

17. A multipolar medical electrode, attachable to the skin of a patient, for deriving electrical signals associated with physiological activity, said electrode comprising:

a thin, flat, flexible pad of nonconductive material having opposite surfaces and having an adhesive on one of said surfaces;

a pair of spaced well members attached to said pad and extending from the other surface thereof, each well member forming a cavity;

a electrolytic gel in each said cavity;

a release backing covering said adhesive surface and enclosing the electrolytic gel within said cavities, said backing being removable for attaching said pad to the skin of the patient by pressing the adhesive on one surface against the skin to bring the gel in each of said cavities into electrical contact with the skin at spaced locations;

a puncturable membrane on each of said well members; and an electrical connector for transmitting differential electrical signals from said well members to an electrical potential measuring instrument and having a body with a width slightly less than the width of the space between said well members; and a pair of spaced conductive prongs having a distal pointed end extending from said body and a proximate end embedded in said body, said prongs being spaced to puncture said membranes when said body is slid between said well members.

* * * * *